United States Patent

Hoftman et al.

[11] Patent Number: 6,024,696
[45] Date of Patent: *Feb. 15, 2000

[54] SIDE WALL SUPPORT SPECULUM

[76] Inventors: Moshe Hoftman, 22205 Dardenne Ave., Calabasas, Calif. 91302; Nir Hoftman, 1559 8th Ave. Apt #1, San Francisco, Calif. 94122

[ * ] Notice: This patent issued on a continued prosecution application filed under 37 CFR 1.53(d), and is subject to the twenty year patent term provisions of 35 U.S.C. 154(a)(2).

[21] Appl. No.: 09/065,768

[22] Filed: Apr. 24, 1998

[51] Int. Cl.[7] .......................................................... A61B 1/32
[52] U.S. Cl. ............................................. 600/224; 600/225
[58] Field of Search ..................................... 600/224, 225, 600/219, 220

[56] References Cited

U.S. PATENT DOCUMENTS

| | | | |
|---|---|---|---|
| 1,014,799 | 1/1912 | Arthur | 600/224 |
| 2,374,863 | 5/1945 | Guttmann | 600/224 |
| 3,736,919 | 6/1973 | Cotey | 600/225 |
| 3,745,992 | 7/1973 | Poirier | 600/225 |
| 4,597,382 | 7/1986 | Perez, Jr. | 600/220 |
| 5,183,032 | 2/1993 | Villalta et al. | 600/224 |
| 5,377,667 | 1/1995 | Patton et al. . | |
| 5,499,964 | 3/1996 | Beck et al. | 600/220 |
| 5,681,265 | 10/1997 | Maeda et al. | 600/224 |

OTHER PUBLICATIONS

Cooper Surgical Winter 1996 Catalog, Cooper Surgical Inc., pp. 18, 28.
Cooper Surgical Spring 1997 Catalog, Cooper Surgical Inc., p. 29.
Leisegang Sales Catalog, "Retractors", p. 23, 1997.

Primary Examiner—Paul J. Hirsch

[57] ABSTRACT

The present invention provides hingeable side wall support blades integral with any of vaginal speculum parts that operatively lie circumferential to the view of the vagina, whereby the side wall support blades are movable from a collapsed position near the top or bottom blade to an upright position to press back the vaginal walls.

15 Claims, 8 Drawing Sheets

Prior Art - Closed

Prior Art - Open

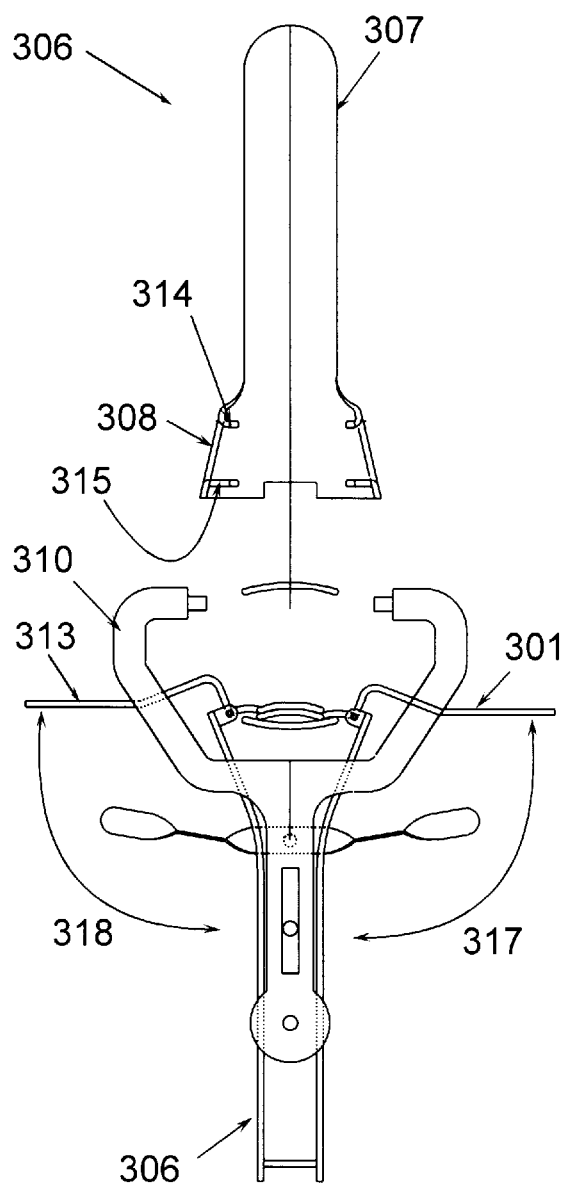
Figure 7
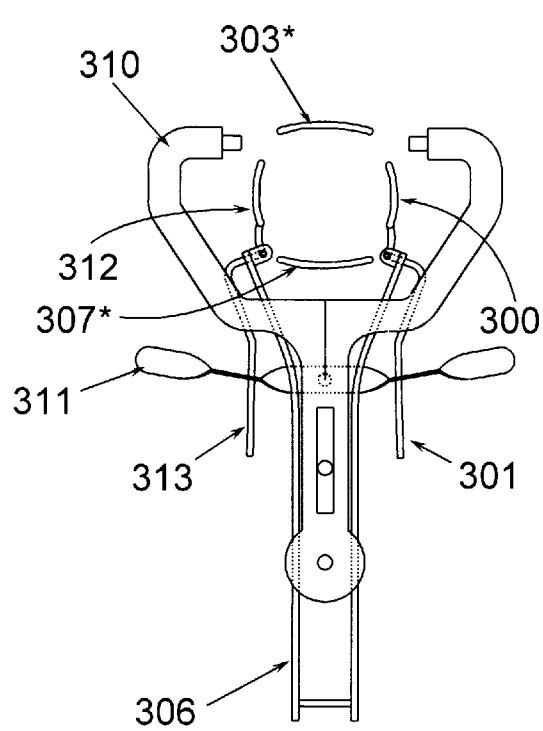
Figure 5
Figure 6

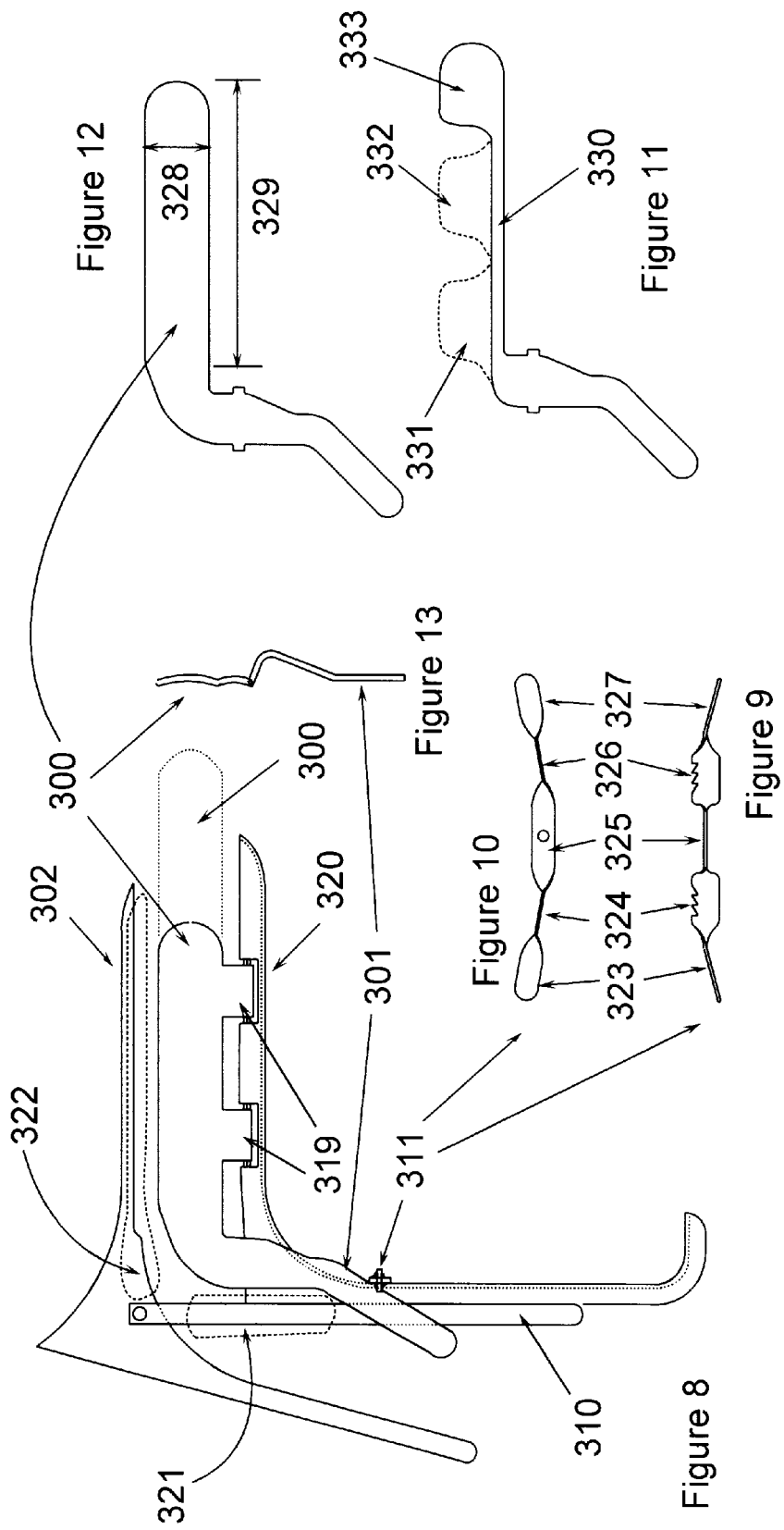

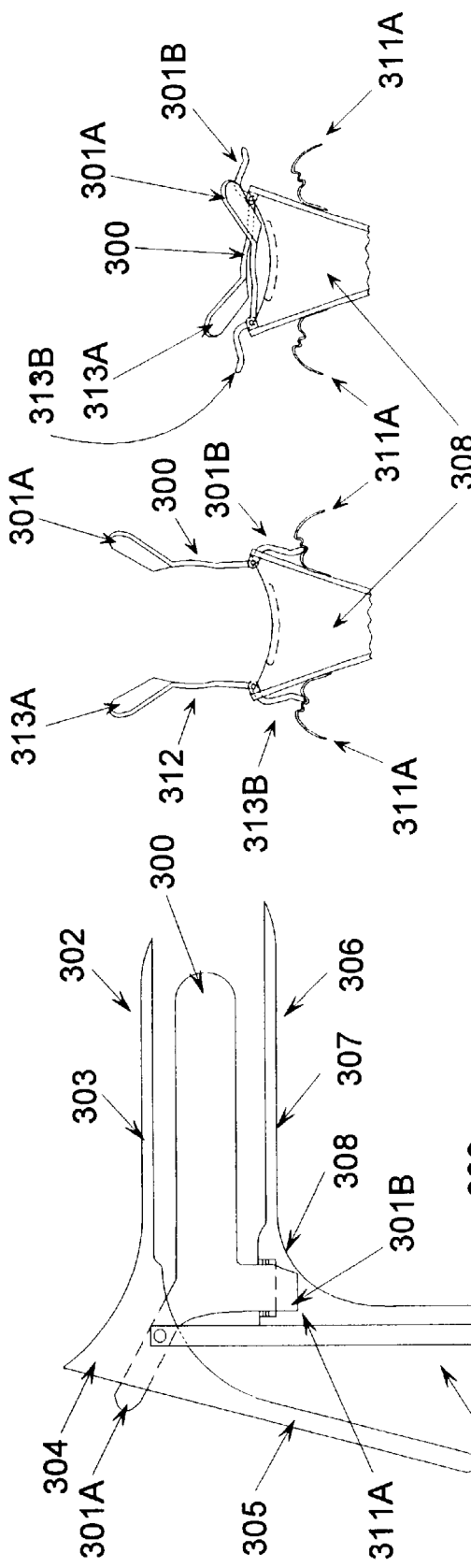

SIDE WALL SUPPORT SPECULUM

BACKGROUND OF THE INVENTION

The present invention relates to medical examination speculums.

It has been known through a very long history of medical speculums that a broadly spatulated, two bladed device is the standard for performing vaginal examinations. Vaginal speculums typical of the current state of the art are found in the Cooper Surgical Winter 1996 catalog of CooperSurgical Inc. at page 18 and in the Cooper Surgical Spring 1997 catalog of CooperSurgical Inc. at page 29. Two bladed lateral wall retractors typical of the current state of the art are shown in the Cooper Surgical Winter 1996 catalog of CooperSurgical Inc. at page 29.

It is a special object of the present invention to address the function of a combined application of a vaginal speculum and a lateral wall retractor shown Cooper Surgical Winter 1996 catalog of CooperSurgical Inc. at the top illustrations of page 18. In that set of illustrations, it is clear that the combined action of the speculum and retractor present a far more effective view of the cervix. The confused and unstable mass of equipment used to achieve that effect is a disadvantage to the skilled examiner. The combination effect on viewing and cervix manipulation is clearly beneficial over the use of a speculum alone, as shown in the comparative illustrations of page 18, i.e., the vaginal walls do not press into the field of view/field of desirable manipulation for stabilization of the cervix. This combined effect is sometimes critical to conducting an effective examination since uteral positioning through retrocession, anteflexion or retroflexion may require maximum viewing/manipulation exposure of the cervix.

U.S. Pat. No. 5,377,667 discloses a vaginal retractor device with side wall supports in the form of a set of relatively narrow top and bottom blades and two pairs of side-directed arms, all of which are under spring tension in the closed position and which equilaterally expand to an open position upon gradual release of the spring tensioning means. This device comprises several disadvantages. The most serious of these is the lack of independent control of the top blade, a defect seen in most of the improvement devices known in the prior art.

As is seen in the Cooper Surgical catalogs, the vaginal speculums all comprise a top spatulate blade capable of angular movement around a base hinge and position locking means (a threaded shaft and positioning nut). Preserving this function is one of the most important aspects of vaginal examination. The bottom blade is maintained in a substantially fixed position while the top blade is moved upward and downward in order to obtain the most effective "presentation" of the cervix. The device of U.S. Pat. No. 5,377,667 cannot perform this function without equilaterally increasing or decreasing the lateral expansion of all the blades and arms at the same time.

The separate lateral wall retractor and two bladed speculum combination suffer from the following disadvantages. Safe manipulation of the top blade of the speculum requires removal from the vaginal vault the lateral wall retractors. The up and down motion of the top blade may pinch or compress a section of the vaginal wall. Removal of the lateral wall retractor is not a minor action. The retractor is of especially heavy construction to facilitate transmission of hand pressure over a curved set of shafts finally to a set of spatulate blades within the vaginal vault. The retractor is also, according to the prices shown in the Cooper Surgical catalogs, 50% more expensive that the vaginal speculum than the retractor is just supposed to be assisting. In addition, the heavy construction of the lateral wall retractor adds to the mass at the lower outside handle area of the examination devices, an effect that has the tendency to "drag" the speculum/retractor combination out of the vaginal vault by a levering action.

It is an object of the present invention to at least effect the function of the combined speculum/retractor apparatus of Cooper Surgical Winter 1996 catalog of CooperSurgical Inc. at page 18. It is further an object of the present invention to present an effective new expansion motion for at least two lateral expansion blades whose axes remain substantially parallel during a first expansion motion.

SUMMARY OF THE INVENTION

The present invention adapts the two blade speculum of the prior art to have one or two side wall supports attached and integral with the speculum, including among the speculum parts with which the side wall supports are optionally movably integral with are at least the top and bottom blades and the yoke. The side wall supports are easily and, in stark contrast to the prior art, independently and separately activated into sidewall support position with finger or thumb pressure. This independent action is achievable due to hinging attachment to the speculum. Since examination of the vaginal wall is an important aspect of vaginal and cervical/uteral examinations, the separately activated wall supports allow the examiner to de-activate the wall support positioning of one side wall support while maintaining the other in place for separate examination and/or manipulation of the one exposed side wall.

In addition, the side wall supports are integral with the speculum and fold down to an effectively view non-obstructive position in the inside (non-vaginal wall facing) depression of the bottom or top blade. Thus, the side wall supports in a folded down (or up in the case of the top blade) position is an insignificant obstacle to new up and down levering manipulation of the top blade or to rotation of the speculum as a whole in the vaginal vault to observe and/or perform procedures on the top and bottom walls of the vagina. It has been found in examinations made with a prototype of the device of the present invention that the easy and extremely convenient availability of independent and separate sidewall supports changes the standard need for extremely broad spatulate top and bottom blades for effective examination. In actual practice, spatulate blade width for the top and bottom blades (or "bill" width as shown in Cooper Surgical Winter 1996 catalog of CooperSurgical Inc. at page 22) has been found to be reducible by up to 60% with side wall supports according to the present invention integrally incorporated into the speculum construction while maintaining the blade length at that required for the patient and/or procedure according to the prior art.

In one embodiment, each side wall support is preferably a relatively narrow, roughly oblate rectangular blade, or its effective equivalent such as a perforated blade or closely joined combination of rods or plates, with a length with an effective longitudinal axis arranged substantially parallel to the length and longitudinal axis of the bottom blade of a speculum. The side wall support blade is preferably hinged at the outer edge of the curved transition section between the top or bottom blade and the handle portion of the blade or along a long edge of the blade. That hinging is preferably attached to or close to the outer edges of the blade or transition section, or within an effective distance from those edges on the top surface (the top surface being that opposed to the top blade) to accomplish the objects of the present invention. The hinging attachment restricts travel of the side wall supports from a collapsed, closed position lying substantially unobstructively flat in the slightly concave depression of the blade to a full support position when the top and bottom blades are separated. The full support position is described in the next paragraph.

A side wall support blade has an integral extension to positioning and, optionally, locking means activatable or deactivatable by thumb and/or finger pressure. Although a less expensive version of these means are adapted to provide a single locking position to a full support position, i.e., with the narrow width of the side wall support blade substantially perpendicular to the bottom blade to effect pressing back of the vaginal wall, it will be apparent to the skilled person with the above disclosure that a several position locking mechanism may also be used to achieve intermediate position locking of the side wall supports or to adapt the levering means attached to the side wall support blade to press beyond substantially perpendicular to the blade section to which it is attached. The single locking position means shown and described in the detailed description may be adapted with pawl and ratchet means such as seen for the lateral wall retractor in the Cooper Surgical Winter 1996 catalog of CooperSurgical Inc. at page 18 to provide a more expensive and heavy means for locking the levering means into position.

It is a further improvement in the art to provide a relatively smaller yoke for the speculum frame to be used with the present invention. The wide yoke advertised as an advantage in the Cooper Surgical Winter 1996 catalog of CooperSurgical Inc. at page 18 is in fact a disadvantage. With the smaller yoke of the present invention, it is unnecessary to provide for the expanding straight or contoured shafts a lateral wall expander and improves the comfort of the examinee whose legs need not be spread as far to accommodate the broad face of a wide flat yoke.

Thus, the present invention makes two dramatic changes for the comfort of the examinee in vaginal exams. First, the initial insertion of the speculum into the vagina is as much or more than 40% easier (with top and bottom blade width reduced to as much or more than 60% of prior art blades). Second, a reduced yoke width means that less flexible examinees need not stretch their legs as much as for prior art speculum frames.

It is also possible, although less preferable, to provide hinging means integral with only the yoke or thereby to adapt any of the speculum parts that operatively lie circumferential to the view of the vagina. It is critical to the present invention only to provide some sort of blade or spatulate means fully or partially capable of pressing back a vagina wall, hinging means between a blade and any of the speculum parts that operatively lie circumferential to the view of the vagina, and levering means that optionally permit locking of the blade into position against the vagina wall.

It is another embodiment of the present invention to provide replaceable blades for the top, bottom and/or side wall support blades. A preferable embodiment includes a U-shaped metal blade support over which a disposable blade may slide into support contact. The open legs of the U-shaped support operatively attach to a transition section between the hinging means and those open legs. In another embodiment of the present invention, the entire speculum/side wall support assembly may be made of coated stainless steel, in a manner known in the art and as shown and described in the Cooper Surgical Winter 1996 catalog of CooperSurgical Inc. at page 21 or with disposable plastic.

The side wall support blades of the present invention comprise several, almost infinite variety of blade outlines within a general field of side wall support on either side of the longitudinal opening created by the opening or separating of the top bottom blades. It is yet a further embodiment of the present invention to provide side wall support blade(s) for a single blade retractor, as are common in the prior art, and will be easily understood as a device similar to the above described two blade speculum whereby the yoke and top blade are removed and the bottom blade device comprises the hinging means for the side wall support blades.

BRIEF DESCRIPTION OF THE DRAWINGS

FIGS. 5 and 6 are operative end views down the lengths of the top, bottom and right and left side wall support blades into an opened position of the top and bottom blades whereby the right and left side wall support blades are locked in an upright support position or folded down in a folded position.

FIG. 7 is a plan view of the bottom blade of the present invention adapted with hinging tabs in a transition section between the handle portion and the bottom blade portion.

FIG. 8 is a side view of the speculum of FIGS. 1 and 2 adapted with a right side wall support blade of the present invention whereby hinging means are provided at a bottom blade outside edge for the right side wall support blade, showing in cross hatching likely hinging means locations on the yoke and top blade edges.

FIGS. 9 and 10 are frontal and top views of the latching means for the levering means of the present invention.

FIGS. 11–15 show various aspects of the several embodiments of the side wall support blades of the present invention. They are all side views, except FIG. 13, which is an end view down the longitudinal axis of the support blade.

FIG. 22 is a side view of the invention device shown in FIG. 3 with substantial changes generally only to the levering means and means with which to latch the side blades into an upright position when manually moved thereto.

FIG. 23 is an end view only of a broken away section of the flared transition section of the lower blade and the side wall blades, levering means and means with which to latch the side blades into an upright position when manually moved thereto when those devices are arranged in an upright position.

FIG. 24 is an end view only of a broken away section of the flared transition section of the lower blade and the side wall blades, levering means and means with which to latch the side blades into an upright position when manually moved thereto when those devices are arranged in a collapsed or closed down position.

DETAILED DESCRIPTION OF THE INVENTION

Figure 1:
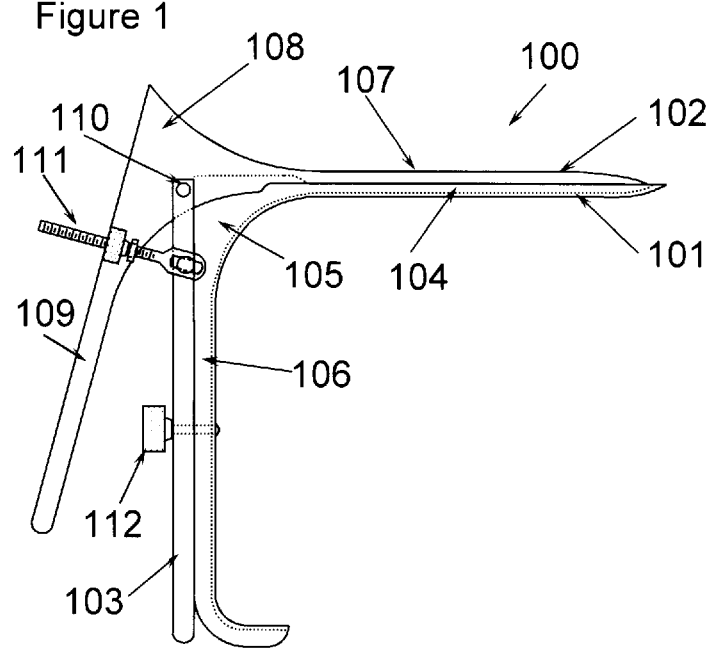
FIGS. 1 and 2 are prior art speculums shown in side view in closed and open positions respectively.

The detailed description of the present invention comprises an assembly and method for using that device in vaginal examination or other similar procedures. The present invention is now discussed with reference to the figures, whose reference numbers indicate substantially similar aspects of the figure when the same reference number is used in separate figures. FIG. 1 shows speculum 100 with a top blade 102 and bottom blade 101 operatively connected by yoke 103. Top blade 102 comprises blade section 107, transition section 108 and handle section 109, whereby section 108 further comprised hinge means 110 to connect with yoke 103. Positioning means 111 permits locking into place up and down levering of the free end of section 107 in a manner most convenient for presentation of the cervix. Bottom blade 101 comprises blade section 104, transition section 105 and handle section 106. Locking nut means 112 provides pressure locking of the slideable connection between yoke 103 and section 106. In the embodiments of the invention positioning means 111 and locking nut means 112 are not shown in the figures to improve understandability, although such devices are understood to be important to the operation of speculum.

Figure 2:
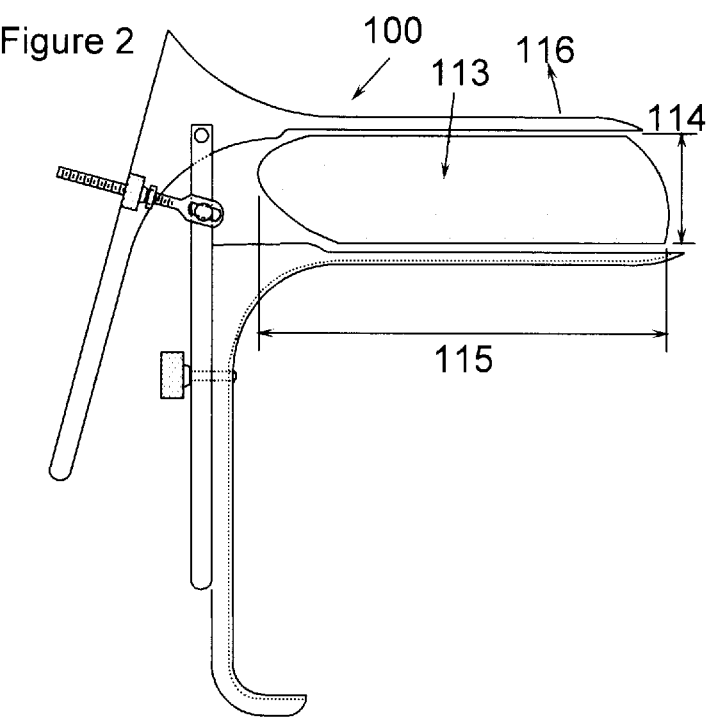

FIG. 2 shows speculum 100 in an open position. The area within which side wall support blades will be effected by the present invention is shown generally as cross hatched section 113, with a length 114 about as long as the top and bottom blade sections and a width 114 defined by the operative opening distance between the top and bottom blade sections. It is for generally part of or entire section 113 that a side wall support blade of the present invention is sought to be applied.

Figure 3:
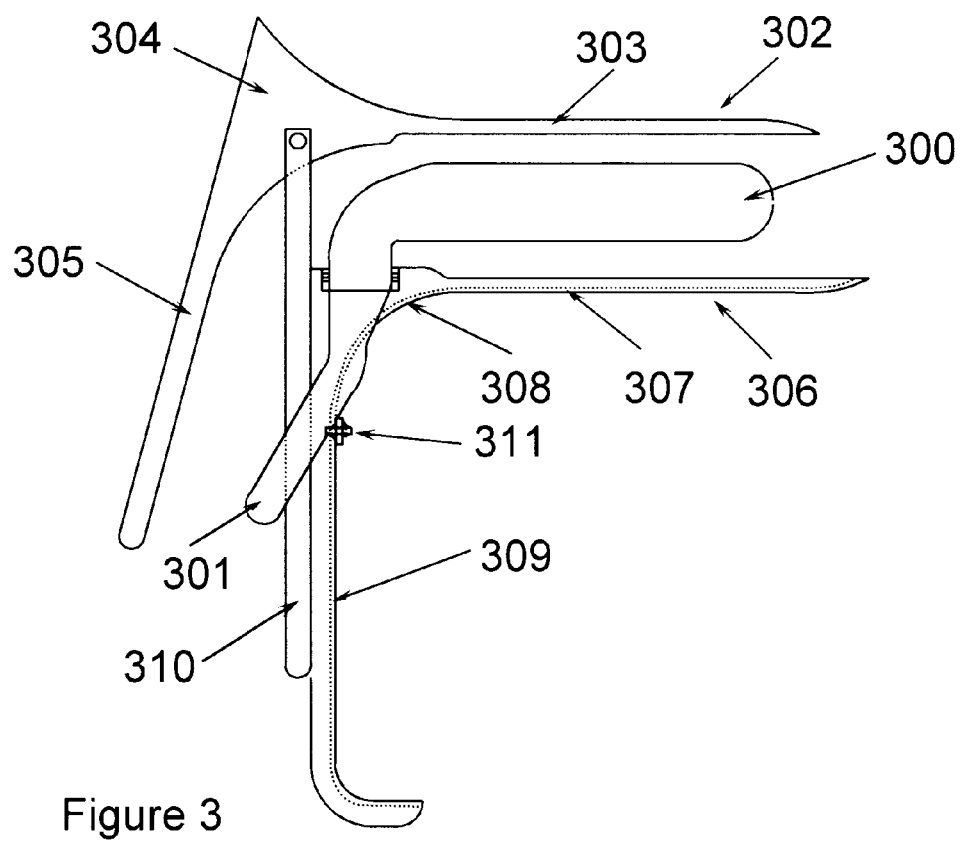
FIG. 3 is a side view of the speculum of FIGS. 1 and 2 adapted with a right side wall support blade of the present invention.

FIG. 3 shows an especially preferred embodiment of the right side wall support blade of the present invention. Top blade 302 comprises blade section 303, transition section 304 and handle section 305. Bottom blade 306 comprises blade section 307, transition section 308 and handle section 309. Yoke 310 provides slidable and upwardly angular motion for section 303 with respect to section 307. Right side wall support blade 300 extends effectively generally over the open section 113 as shown in FIG. 2 to effect substantially complete pressing back of the vaginal wall during an examination and with right side wall support blade 300 in a upright position. Right side wall support blade 300 connects with a transition and hinging section and thereby extends to a levering section 301, which is shown locked in position by latching means 311.

Figure 4:
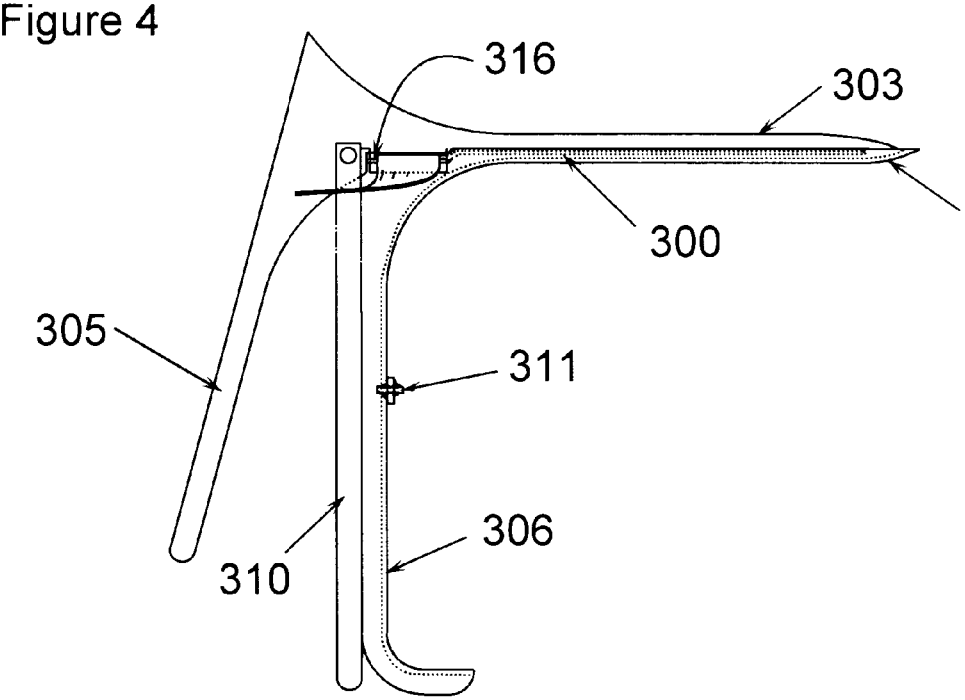
FIG. 4 is a side view of the invention device of FIG. 3 in a closed position with the right side wall support blade lying within a cavity formed from the concavities of the top and bottom blades.

It will be seen that FIG. 4 is a side view of the invention device of FIG. 3 in a position with sections 303 and 307 closed with their inside concavities opposed to form a cavity within which right side wall support blade 300 and the left side wall support blade effectively lies without increasing the combined vaginal insertion thickness of sections 303 and 307. This manner of a closed position for the present invention is the most preferred embodiment, as the combined vaginal insertion thickness of sections 303 and 307 may be somewhat more spaced apart by a relatively thicker or obstructive assembly with the side wall support blades of the present invention while still obtaining most of the benefits of the present invention.

FIG. 5 shows for blades 302 and 306 only a cross section of their sections 303* and 307* respectively for ease of visualization of the view of the vaginal vault to be had with the side wall support blades of the present invention. Left side wall support blade 312 connects with a transition and hinging section and thereby extends to a levering section 313, which is shown locked in position by latching means 311. Thus, the blades 300/312 provide a right/left lateral support while sections 303* and 307* provide top/bottom lateral support. Levering sections 301 and 313 are separately releasable from latching means 311, thereby, as shown in FIG. 6, collapsing blades 300 and 312 to the inside concavity of section 303*, and thereby moving blades 300 and 312 between the upright position in FIG. 5 to the folded down position in FIG. 6 through paths 317 and 318 respectively.

FIG. 7 shows bottom blade 306 with a relatively narrow section 307 and a transition section 308 with hinging lugs 314 and 315 extended from the outer edge of the transition section 308 and drilled with holes to receive small, tab-like lugs 343/344 extending from the edges of the hinging means area between the levering means and the side wall support blade means of the present invention. While this is an extremely simple and effective means by which to effect hinging means between a side wall support blade and the transition section of the bottom blade, the skilled person will recognize with this disclosure that any of the speculum parts that operatively lie circumferential to the view of the vagina that will effect such integral mechanical support are appropriate locations for such hinging means location, with an appropriate adaptation of the hinging means area next to or integral with the side wall support blade.

Figure 16:
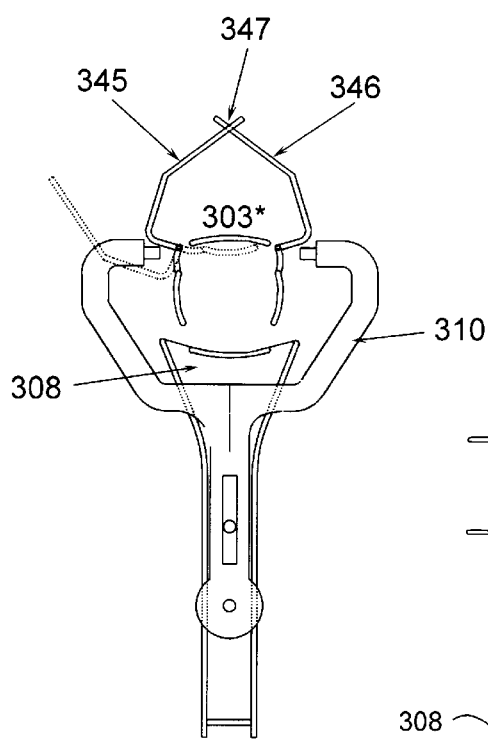
FIG. 16 is an operative end view down the lengths of the top, bottom and right and left side wall support blades into an opened position of the top and bottom blades whereby the right and left side wall support blades are locked in an upright support position or folded down in a folded position and are hinged to the top blade.

Just such optional hinging means and locations are shown in FIG. 8. Hinging means 319 comprise hinging lugs similar to those of FIG. 7 although located along the outside edge of section 307, while the bottom edge of blade 300 is adapted to be extended downward to present to those hinging lugs the small, tab-like lugs similar to those of small, tab-like lugs 343/344. It will be seen that levering means 301 in FIG. 8 are directly connected to blade 300 without a hinging means area interposed between them. FIG. 8 also shows cross hatched areas 321 and 322 which are likely hinging means location areas for integral, rotating and direct or indirect (through a transition section) attachment of the side wall support blades of the present invention, respectively, for the yoke 310 and top blade 302. FIG. 16 shows the side wall support blades 345/346 in an upright position and the left side wall support blade in broken lines in the folded up position, with appropriate levering means adapted to latch together at point 347 to maintain the support blades in position.

FIGS. 9 and 10 show are frontal and top views of the latching means for the levering means of the present invention. Thumb/finger release tabs 323/327 extend from perpendicularly twisted notched sections 324/326, which in turn extend to handle attachment section 325. Section 325 is pierced with a hole through which a pin passes to secure section 325 flat against one side of section 309. The arrangement of the latching means 311 is such that an edge of sections 301 and 313 lock springingly against the notches in sections 324 or 326 and thereby remain latched in position until released by thumb or finger pressure on sections 323 or 327, thereby permitting independent release of either side wall support blade.

Figure 14:
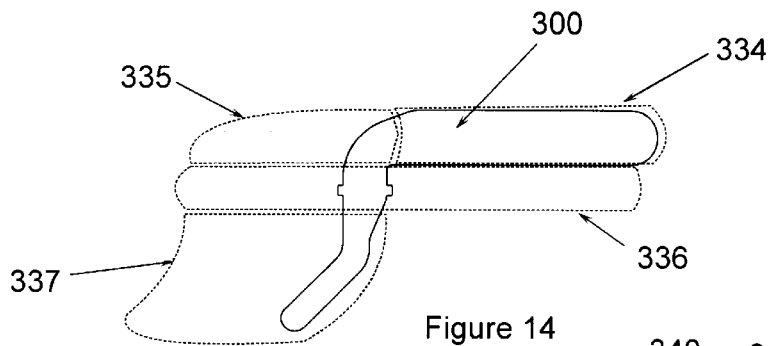
Figure 15:
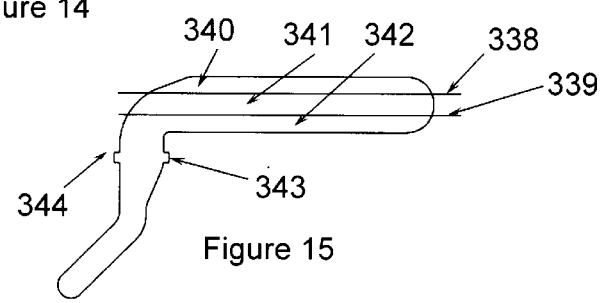

FIG. 14 shows four sections of the embodiment of the side wall support of the present invention, levering means section 337, hinge means section 336, transition section 335 and blade section 334. Section 334 is a broadest extent of the side wall support blade. Section 336 comprises the most appropriate location for hinging means connection of section 334 to the parts of the speculum described above, although transition section 335 may also be appropriate for such location in the case of attachment to the yoke for hinging means. FIG. 12 shows the width 328 of an actual side wall support blade that is at least part of section 334, although that width may be only part of sections 340, 341, or 342 of the side wall support blade outline in FIG. 15, which outline is representative of section 334, such that only a top, middle or bottom section of a potential support field is actually supported with a side wall support blade. In addition, FIG. 11 shows distal support blade 333 supported down the vaginal canal by shaft 330 to provide partial, distal support for the area of the vaginal vault closest to the cervix. Other partial sections 331 and 332 are separate or combined embodiments of partial side wall support blades that will be desirable for partial support of the vaginal wall. In another embodiment of the present invention, a clear acrylic or medically acceptable plastic is preferred for the composition of the top, bottom and/or side wall support blades for viewing the walls of the vaginal canal without collapsing the side wall support blade or moving the top or bottom blades.

In one specific embodiment, width 328 is about 15 mm and length 329 is about 104 mm with a bottom blade length of about 120 mm (from the tip to lug 315) and a width of about 22 mm. The width of the bottom blade is approximately 35% narrower for this prototype than a prior art two "bill" speculum.

Figure 19:
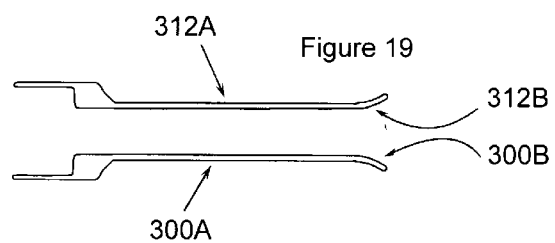
FIGS. 18 and 19 are an end view and top edge views respectively of another embodiment of the side wall support blades, wherein the end of the free end of the blade is curved slightly outward.
Figure 17:
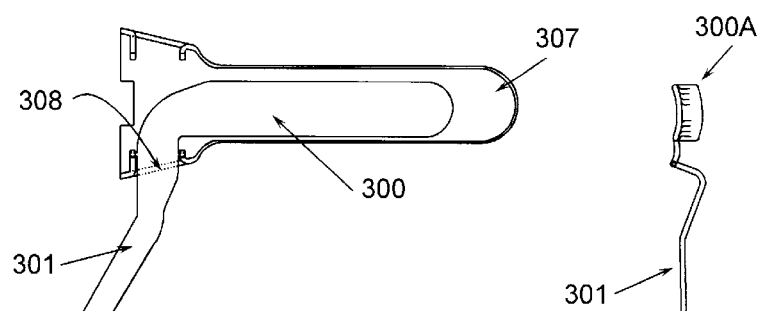
FIG. 17 is a plan view of a right side wall blade folded into a foldedown position within the slight concavity of a bottom blade.
Figure 18:
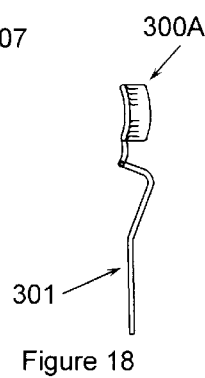

Referring now to FIG. 17, it can be more readily appreciated that blade 300 in a folded down position will effectively lie at least in part in the slight concavity of blade 307. It will also be appreciated that this folded down position may be obtained with hinging means adapted to move the side wall support blades into the slight concavity of the top blade FIGS. 18 and 19 are an embodiment of the side wall support blades with an adaptation to resist removal or slippage of the speculum of the present invention from the vaginal canal. Blades 300A and 312A are substantially similar to blades 300 and 312, with the exception that a slight outward curving 300B and 312B are applied to the free ends of blades 300A and 312B respectively. Sufficient outward deflection of those ends is effected such that there is little damage or discomfort from impression of the deflections into the vaginal wall, while creating a highly effective means for securing the speculum into position therein.

Figure 20:
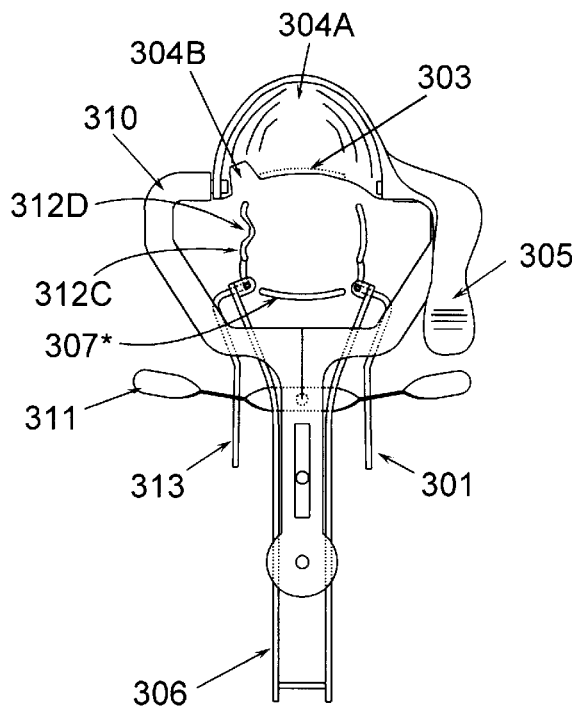
FIG. 20 is an adaptation of a side wall support blade or the transition section of a top blade to move within a notch out or fluted zone a surgical instrument or examination/manipulation device and thereby remove it from the viewing shaft established by the top, bottom and/or side wall support blades.

In an especially valuable improvement over the prior art, the embodiment of the invention shown in FIG. 20 provides a means for removing from a surgeon's or examiner's view (the view being the viewing shaft established by the insertion and moving into an opened position the top, bottom and/or side wall support blades) a surgical instrument or examination/manipulation device. An adaptation of a side wall support blade 312C with a fluted zone 312D or the transition section 304A with a notch out zone 304B of a top blade is made such that a surgical instrument or examination/manipulation device may be situated longitudinally therein and thereby remove it from the view of the surgeon or examiner. The operation of moving a device into the notch out zone 304B comprises first establishing a connection to tissue with the device within the examination cavity and then moving the extension shaft into zone 304B. Although not shown, the prior art discloses many latching devices which may releasably hold the extension shaft of the device in zone 304B, thereby freeing the hand of the surgeon or examiner for other tasks. This is a dramatically important improvement over the prior art, having freed a surgeon's or examiner's hand from simply holding an extension in position.

The operation of moving a device into the fluted zone 312D comprises first, moving side wall support blade 312C into a substantially folded down position, second, establishing a connection to tissue with the device within the examination cavity, third, moving the extension shaft of the device against the left side wall of the vaginal canal, and fourth, moving blade 312D into an opened position, thereby capturing the extension shaft between the surfaces of the fluted zone 312D and the left side of the vaginal canal.

It will be appreciated that notch out zones with or without latching means for the top or bottom blade transition sections and/or fluted zones for the side wall support blades may be provided to effect view-removing positioning and/or securing of the extension shafts of examination or manipulation devices at any point in the periphery established by the top or bottom blades and/or the side wall support blades. The location of the means to effect a view-removing positioning and/or securing function with the speculum of the present invention are in part dependent on the handedness of the surgeon or examiner. Surgeon training typically ignores left handed persons abilities and requires them to learn the procedures in a right handed fashion. A left handed surgeon or examiner will prefer the embodiment of FIG. 20, while a right handed surgeon or examiner will prefer the mirror image location of the view-removing positioning and/or securing means.

Figure 21:
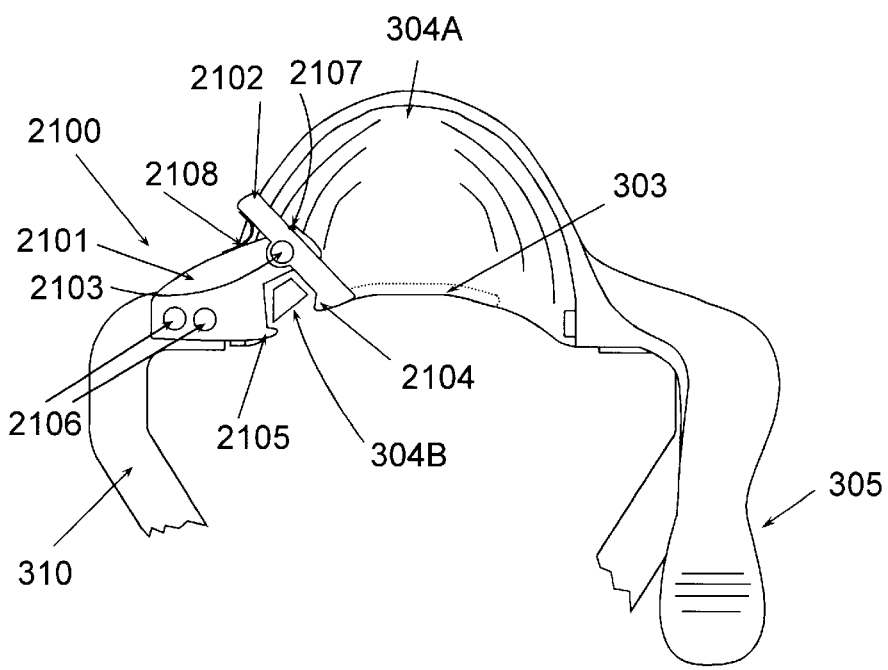
FIG. 21 is an alternate embodiment of the present invention comprising a releasable latching means for instruments used in vaginal or uterine surgical procedures, whereby the latching means support an instrument in the notch out zone of FIG. 20.

The present invention also comprises a releasable latching means for instruments used in vaginal or uterine surgical procedures, whereby the latching means support an instrument in the notch out zone 304B of FIG. 20. FIG. 21 shows one of several equivalent latching means 2100, and the most preferable, by which the extension shaft of a surgical instrument may be releasably held in the notch out zone 304B. Latching means 2100 comprises substantially two plates, a first fixed plate 2101, which is a flat metal or plastic plate adapted to be held in place by pins 2106 such that plate 2101 is substantially parallel to the operator facing side of yoke 310. Plate 2101 comprises an attachment zone providing secure attachment to yoke 310, such teaching thereby intended to and effectively extending means for securing a fixed plate to include attachment of a fixed plate or creation of a similarly integral plate means extending from the edge of notch out zone 304B inwardly within the concavity of surface 304A or effectively nearby on surface 304A such that a fixed plate may be supported by either the yoke or transition zone of the top blade to securingly hold the extension shaft of a surgical device or other such device. Plate 2101 also comprises, in this embodiment, a first opposing lug 2105, adapted to extend slightly into the open effective edge of notch out zone 304B, shown in FIG. 21 to be that space just below the shaded portion of notch out zone 304B.

A second lever plate 2102 is rotatably fixed to plate 2101 by pin 2103. Plate 2102 comprises a second opposing lug 2104 adapted also to extend slightly into the open effective edge of notch out zone 304B, shown in FIG. 21 to be that space just below the shaded portion of notch out zone 304B. Opposing lugs 2104 and 2105 are adapted to extend sufficiently into the aforementioned space so that the distance between them is effectively less than the width of at least one type of surgical or examination instrument. Rotation of plate 2102 about pin 2103 is opposed for counterclockwise motion by spring means 2108, which is preferably strong enough to hold within notch out zone 304B at least one type of surgical or examination instrument against the downward pull of gravity or movement of the patient or other instruments during a surgical or examination procedure. The rotation of plate 2102 in a clockwise motion is opposed by a stop lug 2107 extending just above the flat surface viewed in FIG. 21, thereby leaving notch out zone 304B substantially free of the lug end of plate 2102 for easy insertion and securing of instrument shafts.

It will be understood with the instrument holding embodiment of the present invention that a fixed plate and lever plate may be adapted to operate substantially as described while securing the fixed plate along a bottom edge or other effective portion of transition zone 304. It an alternate embodiment that the fixed plate of the releasable latching means be securely fixed to and/or are integral with the top blade, although the need for angular displacement or movement of the top blade during a procedure requires a similar displacement of the fixed shaft of a surgical or examination device. Such movement may be less preferable in the course of the surgery or examination, necessitating release of the shaft of the surgical or examination device to rotatably move the top blade up or down.

Lever plate means comprise generally spring or latch releasable mechanisms that operate with the fixed plate to hold the shafts of instruments in place near the operator side circumference defined by the transition sections of the top and bottom blades and the sides of the upper portion of the yoke. The mechanism shown in FIG. 21 is one of several that will accomplish the objects of the present invention, generally to provide securing means for instruments typically held in place by hand in vaginal surgeries or examinations.

This instrument holding embodiment of the present invention comprises a speculum with only a latching means without a notch out zone on the upper blade. The shaft of the instrument may still be effectively directed substantially parallel to the longitudinal axis of the top or bottom blade depending on whether the fixed plate is integral with the yoke upper portion/bottom blade transition section or top blade transition section respectively. It is more preferable to provide a notch out zone in the inside, blade opposing edges of the transition sections of the top or bottom blades to cooperate with the latching means in providing a means and method for removing the shaft of an instrument from the viewing window created by the speculum blades. The surgeon or examiner clearly obtains thereby freedom from holding that instrument in position.

Another embodiment of the present invention is now discussed with reference to FIGS. 22–24. FIG. 22 is a side view of the invention device shown in FIG. 3 with substantial changes generally only to the levering means and means with which to latch the side blades into an upright position when manually moved thereto. FIG. 23 is an end view only of a broken away section of the flared transition section of the lower blade and the side wall blades, levering means and means with which to latch the side blades into an upright position when manually moved thereto when those devices are arranged in an upright position. FIG. 24 is an end view only of a broken away section of the flared transition section of the lower blade and the side wall blades, levering means and means with which to latch the side blades into an upright position when manually moved thereto when those devices are arranged in a collapsed or closed down position. In general, this embodiment is a dramatic improvement in arrangement, access, and patient safety over the embodiment shown in FIG. 3. The hinging means are those of the embodiment of FIG. 3, although the levering means 301/313 of FIG. 3 are truncated to form latching tips 301B/313B, while the levering means 301A/313A comprise the means for moving the blades 300/312 from a closed or collapsed position shown in FIG. 24 to the upright or opened position in FIGS. 22 and 23. It is intended that no portion of the levering means 301A/313A in their paths from an upright to a collapsed position should normally contact the patient, as opposed to the levering means of FIG. 3 which might abrade against the patient's inner thigh skin surface in moving the side wall blades from a collapsed to an upright position if the speculum were to be inserted substantially for its entire blade length. The side view of levering means 301A in FIG. 22 clearly indicates that a free end extends beyond the extent of the side view of the flared transition section 304 of the upper blade 302. Although this side view extension length is preferable for easy access to move the levering means from a collapsed to an upright position, such levering means 301A separately from or substantially the same as levering means 313A may have different such side view extension lengths depending on the procedures to be performed, the handedness of the examiner, and other such considerations. It will be appreciated that an equivalent performance for side wall support is achieved with this embodiment of the present invention as that of the device of FIG. 3 described above. Latching means 311A comprise spring quality metal or plastic attachments to the outer surface of the flared transition section 308 of lower blade 306 and are adapted to securingly engage latching tips 301B/313B. The materials and attachment of latching means 311A should be sufficient to resist displacement of the latching tips 301B/313B from their securement so that sidewall blades 300/312 maintain an upright position when locked into place as shown in FIG. 23.

Figure 25:
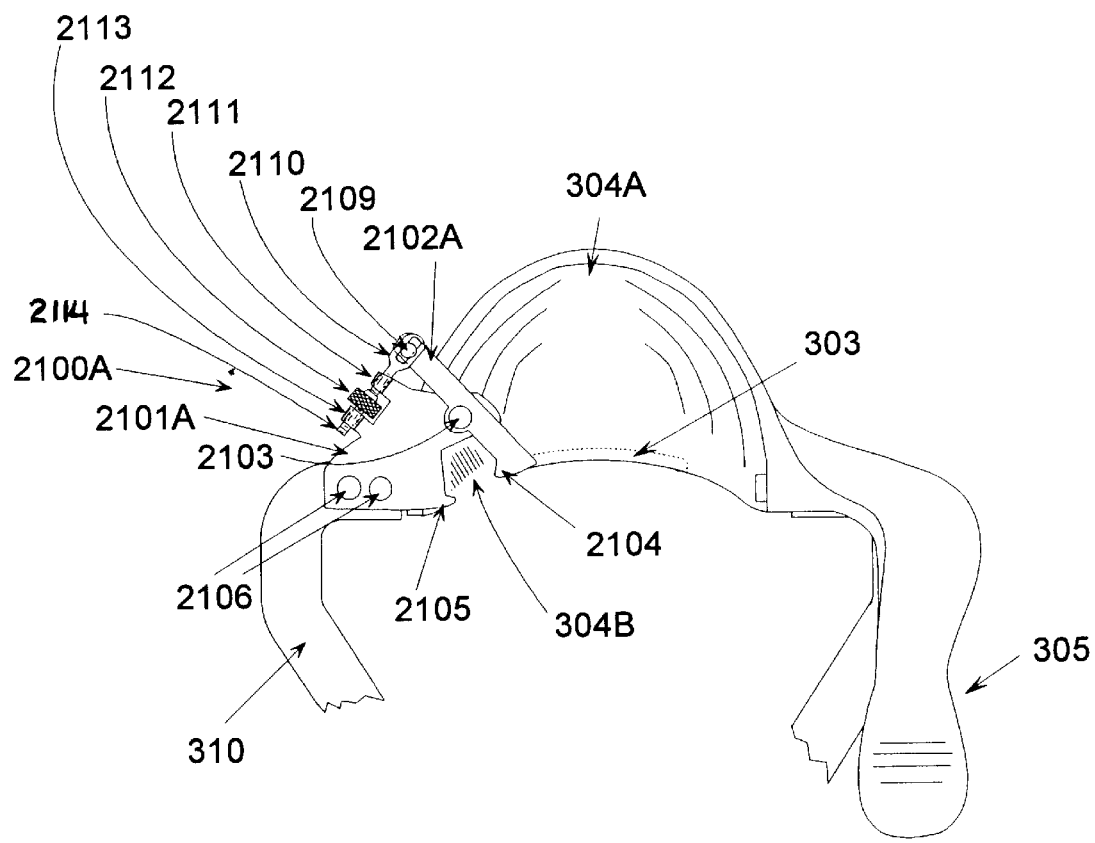
FIG. 25 is an alternate embodiment of the present invention comprising a releasable latching means for instruments used in vaginal or uterine surgical procedures, whereby the latching means support an instrument in the notch out zone of FIG. 20.

Another embodiment of the present invention is now discussed with reference to FIGS. 25. As well similarly described and shown in FIG. 21, the present invention is adaptable for installation of an instrument/tube holder that may support away from the field of view down the longitudinal length of the blades shafts of instruments and/or tubes for fluid flooding or evacuation. The instrument/tube holder 2100A of FIG. 25 comprises the substantially flat plate 2101A attached to yoke 310 with pins 2106, whereby the plate 2101A is extended in an upper portion upwardly with two relatively narrow finger-like projections. Those projections are then bent and curled in the direction of the viewer observing FIG. 25 and bent over still further until a tip of the projection approaches the surface of plate 2101A to form two shaft retaining projections 2111 and 2113 adapted to accommodate a loose but retaining fit for threaded shaft 2113. Shaft 2113 extends through the preferably cylindrical internal voids of projections 2111 and 2113 to slotted end 2110, which is a small flattened plate with a slot in it, the slot being adapted to have slideable within it the shaft portion of a headed pin extension 2109 extending from an extended portion of handle 2102A. This headed pin extension/slotted end 2110 is substantially as shown in FIG. 2 with respect to the upper blade adjustment means, although the present embodiment comprises securing means on either side of a knurled nut 2112, which is rotatable about threaded shaft 2114. The effect of providing this embodiment's improvements over the embodiment of FIG. 21 is that a single finger rotation of nut 2112 will cause threaded shaft 2114 to be forced along a common axis of the internal voids of projections 2111 and 2113 and therefore results in handle 2102A rotating about pin 2103, forcing to a new and fixed position the projection 2104 either toward or away from an instrument shaft or tube to be retained in zone 304B. The instrument holder of this embodiment may be efficiently used without notching out the upper blade, i.e., although the angle of deflection of the retained shaft or tube may be less preferably increased, such a shaft or tube will still be advantageously retained away from the retractor user's field of view. Although not shown, the present instrument holder of the present invention is a capable of being detached from yoke 310 and attached via plate 2101A on the surface opposite the one shown in FIG. 25 to a clamp or clamps, opposing flexible blades or the like comprising detachable attachment means to releaseably attach the instrument holder of the present invention to transition section of the upper blade. Such a development will allow the user to secure to near the edge of the transition section of the upper blade the instrument holder of the present embodiment or that of FIG. 21 before or after the speculum is in place for examination of a patient.

Those design options will sometimes present the designer with considerable and wide ranges from which to choose appropriate process modifications for the above examples. However, the objects of the present invention will still be obtained by the skilled person applying such design options in an appropriate manner.

We claim:

1. A vaginal expander comprising:
(a) top and bottom blades of substantial width along their lengths adapted to be held together facing each other for insertion into a vagina and connected to means to move the top and bottom blades apart relative to each other in a substantially directly opposing relationship, such that the bottom blade is maintainable in a lower position while the top blade is movable upward therefrom to form an open position, whereby the bottom blade comprises a first blade section having two long edges, a longitudinal axis, an inside surface, and an outside surface adapted to be inserted into a vagina and oppose a vaginal canal surface; and
(b) a first side wall support blade with a length generally parallel to the longitudinal axis is adapted to be connected to a first hinging means substantially rotationally parallel with the longitudinal axis of the first blade section whereby the first side wall support blade may be rotated about the first hinging means from a first position generally parallel to the longitudinal axis and close to the inside surface to a second position generally parallel to the longitudinal axis but providing side wall support during a vaginal exam when the top and bottom blades are in the open position.

2. The expander of claim 1 wherein the first hinging means connects the first side wall support blade to a first of the two long edges of the first blade section.

3. The expander of claim 1 wherein the first blade section further comprises a slight concavity along the longitudinal axis of the inside surface such that when the first side wall support blade is in the first position the first side wall support blade lies at least in part within the slight concavity.

4. The expander of claim 1 wherein the first side wall support blade is adapted to be rotatable about the first hinging means to the second position such that the first side wall support blade is substantially perpendicular with or at an obtuse angle with respect to the first blade section.

5. The expander of claim 1 wherein a second side wall support blade has a length generally parallel to the longitudinal axis is adapted to be connected to a second hinging means substantially rotationally parallel with the longitudinal axis of the first blade section whereby the second side wall support blade may be rotated about the second hinging means from a third position generally parallel to the longitudinal axis and close to the inside surface to a forth position generally parallel to the longitudinal axis but providing side wall support during a vaginal exam when the top and bottom blades are in the open position, such that the second side wall support blade in the fourth position opposes the vaginal wall supportable by the first side wall support blade in the second position.

6. The expander of claim 5 wherein a first and second levering means are respectively connected to the first and second side wall support blades and are adapted to rotate by finger pressure the first and second side wall support blades about their respective hinging means.

7. The expander of claim 6 wherein a first latching means are provided and are adapted to secure the first levering means such that the first side wall support blade is fixed in a vaginal wall pressing position.

8. The expander of claim 6 wherein a second latching means are provided and are adapted to secure the second levering means such that the second side wall support blade is fixed in a vaginal wall pressing position.

9. The expander of claim 6 wherein the second hinging means connects the second side wall support blade to the second of the two long edges of the first blade section.

10. The expander of claim 5 wherein the first blade section comprises two ends, a first end adapted to be inserted into a vagina and a second end, the second end being connected to a transition section comprising two transition edges and a transition inside surface whereby the first hinging means connects the first side wall support blade to a first of the two transition edges.

11. The expander of claim 10 whereby the second hinging means connects the second side wall support blade to the second of the two transition edges.

12. A vaginal expander comprising:
(a) top and bottom blades of substantial width along their lengths adapted to be held together facing each other for insertion into a vagina and connected to means to move the top and bottom blades apart relative to each other in a substantially directly opposing relationship, such that the bottom blade is maintainable in a lower position while the top blade is movable upward therefrom to form an open position, whereby the top blade comprises a first blade section having two long edges, a longitudinal axis, an inside surface, and an outside surface adapted to be inserted into a vagina and oppose a vaginal canal surface; and
(b) a first side wall support blade with a length generally parallel to the longitudinal axis is adapted to be connected to a first hinging means substantially rotationally parallel with the longitudinal axis of the first blade section whereby the first side wall support blade may be rotated about the first hinging means from a first position generally parallel to the longitudinal axis and close to the inside surface to a second position generally parallel to the longitudinal axis but providing side wall support during a vaginal exam when the top and bottom blades are in the open position.

13. The expander of claim 12 wherein the first blade section further comprises a slight concavity along the longitudinal axis of the inside surface such that when the first side wall support blade is in the first position the first side wall support blade lies at least in part within the slight concavity.

14. The expander of claim 12 wherein a second side wall support blade has a length generally parallel to the longitudinal axis is adapted to be connected to a second hinging means substantially rotationally parallel with the longitudinal axis of the first blade section whereby the second side wall support blade may be rotated about the second hinging means from a third position generally parallel to the longitudinal axis and close to the inside surface to a forth position generally parallel to the longitudinal axis but providing side wall support during a vaginal exam when the top and bottom blades are in the open position, such that the second side wall support blade in the fourth position opposes the vaginal wall supportable by the first side wall support blade in the second position.

15. The expander of claim 14 wherein a first and second levering means are respectively connected to the first and second side wall support blades and are adapted to rotate by finger pressure the first and second side wall support blades about their respective hinging means.

* * * * *